United States Patent [19]

Demain et al.

[11] 4,178,210

[45] Dec. 11, 1979

[54] ACELLULAR SYNTHESIS OF CEPHALOSPORINS

[75] Inventors: Arnold L. Demain, Wellesley, Mass.; Masanobu Kohsaka, Osaka, Japan

[73] Assignee: Massachusetts Institute of Technology, Cambridge, Mass.

[21] Appl. No.: 880,036

[22] Filed: Mar. 17, 1978

Related U.S. Application Data

[63] Continuation-in-part of Ser. No. 775,156, Mar. 7, 1977, abandoned.

[51] Int. Cl.$^2$ ............................................. C12D 9/00
[52] U.S. Cl. .................................... 435/47; 435/926
[58] Field of Search .................. 195/36 C, 29, 77, 81

[56] References Cited

U.S. PATENT DOCUMENTS 3,825,473  7/1974  Gargiuolo ........................... 195/36 R

OTHER PUBLICATIONS

E. P. Abraham, Biosynthesis and Enzymatic Hydrolysis of Penicillins and Cephalosporins, University of Tokyo Press, pp. 12–17.
S. W. Drew et al., The Obligatory Role of Methionine in the Conversion of Sulfate to Cephalosporin C, European Journal of Applied Microbiology, 2, 1975, pp. 121–128.
A. Demain, Biochemistry of Penicillin and Cephalosporin Fermentations, Lloydia, vol. 37, No. 2 (1974).
Morin et al., Chemistry of Cephalosporin Antibiotics III, Chemical Correlation of Penicillin and Cephalosporin Antibiotics, J. Amer. Chem. Soc., 85, (1963), pp. 1896–1897.
Patricia Fawcett et al., Aspects of Cephalosporins and Penicillin Biosynthesis, Academic Press, pp. 129–138.
Brenda Smith et al., Biosynthesis of Penicillin and Cephalosporin C, Biochem. J. 103, pp. 877–890 (1967).
Kitano et al., Agr. Biol. Chem., 38(9), pp. 1761–1762, 1974.

*Primary Examiner*—Raymond N. Jones
*Assistant Examiner*—Robert J. Warden
*Attorney, Agent, or Firm*—Arthur A. Smith, Jr.; Anthony M. Lorusso

[57] ABSTRACT

A cephalosporin antibiotic is produced from a precursor comprising the five membered thiazolidine ring and the $\beta$ lactam moiety characteristics of penicillins by contacting the precursor with a cell-free extract of *Cephalosporium acremonium* in the presence of ATP under conditions favoring high oxygen transfer. Preferably, an ATP regeneration system comprising a phosphate donor and a phosphotransferase enzyme is included in the reaction.

10 Claims, 1 Drawing Figure

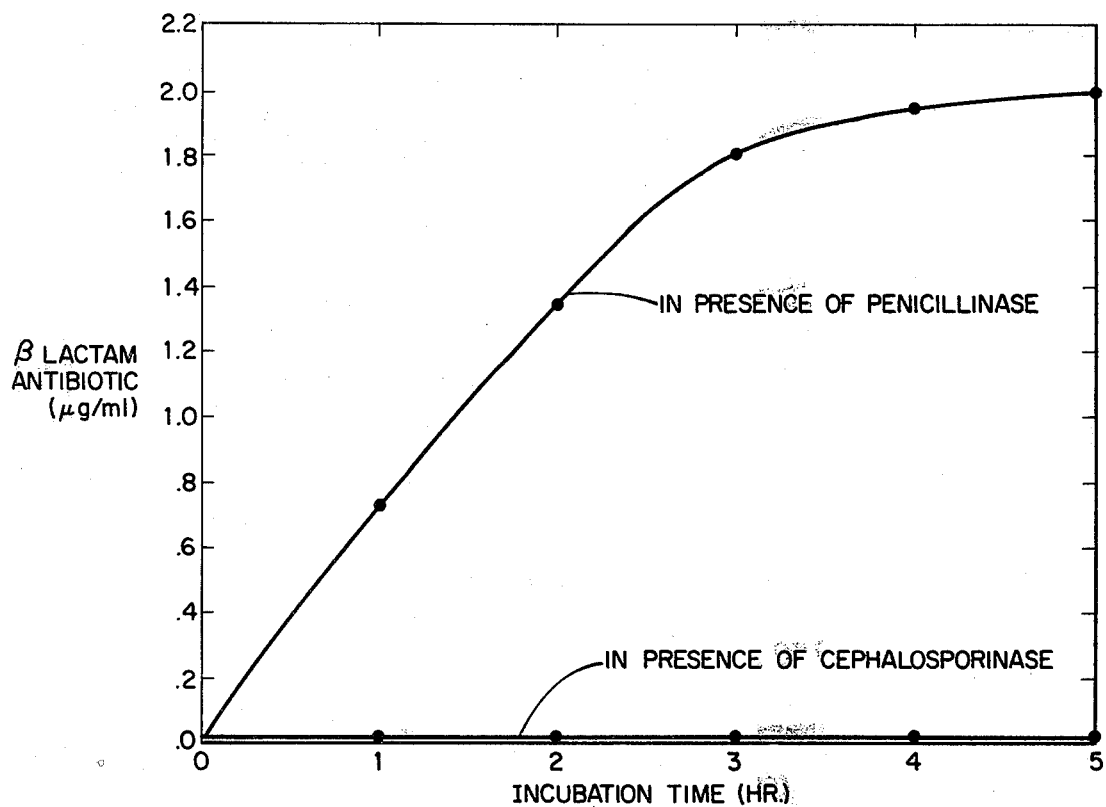

ACELLULAR SYNTHESIS OF CEPHALOSPORINS

The Government has rights in this invention pursuant to Grant No. BMS-75-17527 awarded by the National Science Foundation.

REFERENCE TO RELATED APPLICATION

This application is a continuation-in-part of related U.S. application Ser. No. 775,156 entitled "Acellular Synthesis of Cephalosporins," filed Mar. 7, 1977 now abandoned.

BACKGROUND OF THE INVENTION

This invention relates to a cell-free process for producing a cephalosporin antibiotic.

Cephalosporins comprise a group of β lactam penicillin-like antibiotic substances which are soluble in water and exhibit activity against certain penicillin resistant staphylococci. Examples of cephalosporin antibiotics include desacetylcephalosporin C, deacetoxycephalosporin C, 7 methoxy cephalosporin C, cephamycin A and B, and cephalosporin C. The latter has the structural formula:

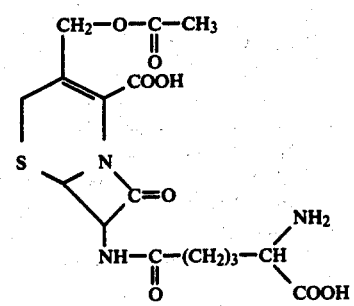

Penicillin N, an example of a related family of antibiotics, has the structure set forth below:

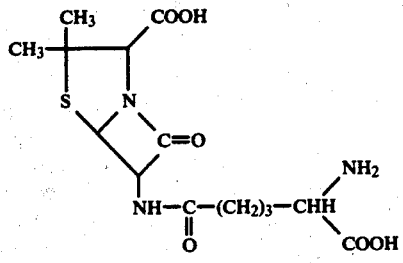

A review of the structural formulae of the above noted β lactam compounds indicates that it would be theoretically possible to convert penicillins such as penicillin N to cephalosporins if the five membered thiazolidine ring of the penicillins could be expanded to the six membered dihydrothiazine ring characteristic of the cephalosporins. Indeed, in the Journal of American Chemical Society, Vol. 85, at pages 1896 and 1897, R. B. Morin et al. disclose a method of synthetically producing a cephalosporin from a penicillin.

It is also known that *Cephalosporium acremonium* (*C. acremonium*) can synthesize both penicillin N and cephalosporin C by fermentation. In this process, the amino acids L-α-aminoadipic acid, L-valine, and L-cysteine are formed by the culture and used as precursors. The antibiotic activity of both cephalosporin C and penicillin N can be destroyed if they are treated with cephalosporinase, an enzyme which is prepared from *Enterobacter cloacae*. Penicillinase, a commercially available enzyme, destroys the antibiotic activity of penicillin N but has no detectable effect on the cephalosporins.

As used throughout this specification and claims, the term "cephalosporin" will thus refer to a β lactam antibiotic substance which loses its antibiotic activity when exposed to cephalosporinase but is not affected by penicillinase.

SUMMARY OF THE INVENTION

In accordance with the invention, it has been discovered that cephalosporins can be made in a cell-free process by exposing certain substances characterized by the five membered thiazolidine ring and the β lactam moiety of penicillins to a cell-free extract of *C. acremonium* in the presence of adenosine triphosphate (ATP) under conditions favoring high oxygen transfer. While the exact identity of the cephalosporin or cephalosporins produced has not as yet been determined, it is clear that the product or products have antibiotic properties identical to those of known cephalosporins such as cephalosporin C.

The substances which are useful as starting materials have the formula:

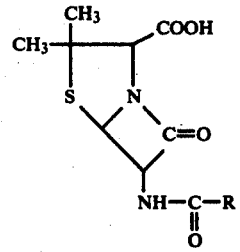

where R is a hydrocarbon containing 1-4 carbon atoms terminally substitued with a radical selected from the group consisting of carboxy, amino, and combinations thereof. The preferred starting materials are those wherein R is:

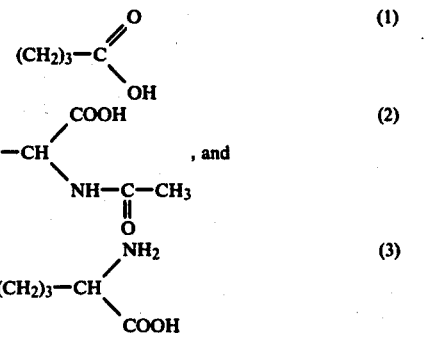

As to (3), only the D-form; penicillin N, has been found to be active as a starting material.

In the preferred process of the invention, an ATP regenerating system comprising a phosphate donor and a phosphotransferase enzyme is included with the starting material and the extract to optimize cephalosporin production. Preferably, the phosphate donor is phosphoenolpyruvate (PEP) and the phosphototransferase enzyme is pyruvate kinase. The cell-free extract of *C. acremonium* is preferably produced by enzymatic lysis of the cells with, for example, known enzyme preparations such as Cytophaga lytic enzyme L₁ and Zymolyase from *Arthrobacter luteus*, and then homogenizing the resulting protoplasts. Also, it is necessary to vigorously shake the reaction solution or otherwise effect efficient oxygen transfer.

Accordingly, it is an object of the invention to provide a cell-free process for producing a cephalosporin antibiotic.

Another object of the invention is to produce cephalosporin without resorting to fermentation procedures or laboratory synthesis.

Another object of the invention is to produce cephalosporins in significant quantities by including an energy generating system comprising a phosphate donor and a phosphotransferase enzyme in the cell-free enzymatic process.

Still another object of the invention is to provide a method of preparing cell-free extracts of *C. acremonium* capable of synthesizing cephalosporins.

BRIEF DESCRIPTION OF THE DRAWING

The sole FIGURE of the drawing is a graph of β lactam antibiotic produced in μg/ml vs. incubation time and assayed in the presence of penicillinase or cephalosporinase.

DESCRIPTION OF THE PREFERRED EMBODIMENT

In accordance with the invention, a precursor to cephalosporin is intimately contacted with a cell-free extract, made from *C. acremonium*, in the presence of ATP and is thereby transformed by one or more enzymes in the extract to a cephalosporin antibiotic. *C. acremonium* is a well known microorganism, and several strains are available from the American Type Culture Collection such as ATCC 20339 (Cephalosporium sp. strain F. 12) and ATCC 14553.

The preferred method of preparing the cell-free extract comprises lysing a protoplast pellet made from whole cells obtained from 52-56 hr. mycelia and treated with, e.g., Cytophaga lytic enzyme L₁ preparation and Zymolyase-5000. After treatment with the enzymes, the protoplast pellet suspension is centrifuged and gently homogenized. A second centrifugation enables separation of a supernatant liquid extract which may be used to produce the cephalosporins. Thus, if a suitable starting material is mixed with this cell-free extract, and the mixture is vigorously agitated, a cephalosporin rich solution results.

The substances which are useful as starting materials have the formula:

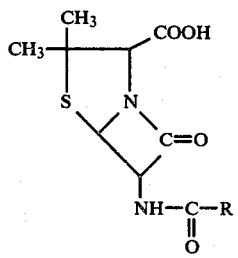

where R is a hydrocarbon containing 1-4 carbon atoms terminally substituted with a radical selected from the group consisting of carboxy, amino, and combinations thereof. The preferred starting materials are those wherein R is:

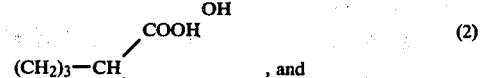

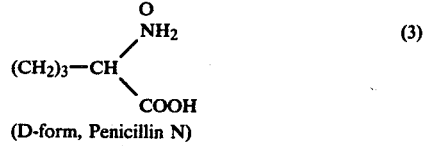

(D-form, Penicillin N)

It has further been discovered that the addition of ATP, and especially ATP plus an ATP regeneration system, increases the amount of cephalosporin produced. The ATP regenerating system comprises a phosphate donor and a phosphotransferase enzyme. The preferred phosphate donor is phosphoenolpyruvate and its corresponding phosphotransferase enzyme, pyruvate kinase. However, it will be appreciated that other phosphate donor-phosphotransferase enzymes may also be used. These include but are not limited to phosphotransferases such as creatine kinase, acetate kinase, carbamate kinase, phosphoramidate kinase, arginine kinase, 3-phosphoglycerate kinase, and aspartate kinase, and corresponding phosphate donors such as creatine phosphate, acetyl phosphate, carbamyl phosphate, phosphoramidate, arginine phosphate, 1,3-diphosphoglycerate, and aspartyl phosphate.

While the exact identity of the one or more cephalosporins produced in this reaction is presently unknown, the presence of a cephalosporin can be verified with the aid of three agents: a mutant of either *Escherichia coli* (designated ESS) or certain strains of *Pseudomonas aeruginosa* IFO 3080 (see Agr. Biol. Chem., 38(9), 1761-1762, 1974) which are supersensitive specifically to β lactam antibiotics; penicillinase, an enzyme which destroys the antibiotic properties of penicillin N; and cephalosporinase, an enzyme which destroys the antibiotic properties of both cephalosporins and penicillin N. The cell-free system of the invention has been observed to produce antibiotics which are effective against ESS or the *P. aeruginosa*, and thus were determined to contain the β lactam moiety. However, the antibiotic activity of the product was unaffected by the presence of penicillinase, but destroyed by cephalosporinase. Accordingly, it is clear that a β lactam cephalosporin antibiotic was being produced.

The possibility that intact cells are responsible for the biosynthesis has been eliminated. It has been found that when agitation is low, cephalosporin production ceases, indicating that oxygen transfer is important to the synthesis. The addition of cycloheximide has been observed to have no effect on the procedure, indicating that protein synthesis is not required for the cephalosporin production. Addition of the precursors to the known fermentation production, L-α-aminoadipic acid, L-valine, and L-cysteine, had no observable effect on the cephalosporin production. While the presence of penicillins, particularly Penicillin N, enhances cephalosporin production, penicillin G or 6 amino-penicillanic acid showed no stimulatory activity. If penicillinase is added to the cell-free system during the course of the reaction, cephalosporin production is immediately terminated.

In view of the above, it is apparent that the cell-free extract contains one of more specific enzymes which require a precursor containing the five membered thiazolidine ring and the β lactam moiety. The invention will be further understood from the following non-limiting example.

EXAMPLE

Cultures of C. acremonium were incubated at 25° C. in 250 ml flasks containing 40 ml samples of a medium consisting of the ingredients set forth below. The specific C. acremonium used in this example was originally obtained from Eli Lilly and Co. and is available on an unrestricted basis under the designation of MIT-M4 on request directed to the Department of Nutrition and Food Science, Massachusetts Institute of Technology, Cambridge, Mass. 02139.

| Cephalosporium acremonium production medium | |
|---|---|
| Sucrose | 36.0 g |
| Glucose | 27.0 g |
| $(NH_4)_2SO_4$ | 7.5 g |
| Oleic acid | 1.5 g |
| Salt #1 | 7.5 ml |
| Salt #2 | 135.0 ml |
| Methionine | 3.0 g |

These ingredients were solubilized in enough pH 7.3 buffer to make up 1 liter of solution. Salt #1 comprises a 20 g/l solution of ferrous ammonium sulfate .6H$_2$O. Salt #2 comprised a mixture of the ingredients set forth below dissolved in enough water to make 1.8 liters of solution.

| Salt #2 | |
|---|---|
| $K_2HPO_4$ | 208.0 g |
| $KH_2PO_4$ | 204.0 g |
| $Na_2SO_4 . 10H_2O$ | 22.7 g |
| $MgSO_4 . 7H_2O$ | 4.9 g |
| $ZnSO_4 . 7H_2O$ | 0.4 g |
| $MnSO_4 . H_2O$ | 0.4 g |
| $CuSO_4 . 5H_2O$ | 0.1 g |
| $CaCl_2 . 2H_2O$ | 1.0 g |

The mycelium harvested at 52–56 hours was filtered and washed 3 times with 20 ml samples of distilled water. The dampdry mycelium was resuspended in 10 ml of citrate-phosphate buffer (pH 7.3), McIlvaine's, (containing 0.01 M dithiothreitol) and incubated for 1 hour at 28° C. with shaking. After filtering and washing, the mycelium was resuspended in the same buffer, this time containing 1.0 M NaCl, 0.02 M MgSO$_4$ and 40 mg of the lysing preparation Cytophaga lytic enzyme L$_1$ and 40 mg Zymolyase-5000 from Arthrobacter.[Cytophaga lytic enzyme L$_1$ was obtained from BDH chemicals, Poole, Dorset U.K. The preparation of this enzyme is described in British Pat. No. 1,048,887 and originally was isolated from the culture medium of a micro-organism temporarily designated L$_1$. This organism has been deposited in the National Collection of Industrial Bacteria in Aberdeen, Scotland as N.C. I.B. 9497. The lytic enzyme L$_1$ preparation has been described as having endoβ(1→3) and endoβ(1→4) glucanase activites. (Biochemical Journal, Vol. 135, p. 11 et seq.) (1973) (Manners, D. J. and Wilson, G.)] [Zymolyase-5000, herein referred to as Zymolyase, was obtained from Kirin Brewery Co., Ltd., Takasaki, Gumma Pref, Japan. Zymolyase-5000 is an enzyme preparation produced by a submerged culture of Arthrobacter luteus, which effectively lyses cell walls of viable yeast cells. As supplied by Kirin, Zymolyase-5000 contains the enzyme Zymolyase and may also contain β-1,3 glucanase (EC3, 2, 1, 39), mannase, protease and acid phosphatase, etc. The preparation of Zymolyase has been described in Archives of Biochemistry and Biophysics, vol. 153, p. 403 (1972) (Kitamura, K., and Yamamoto, Y.).] The suspension was incubated at 28° C. for 3 hours with shaking. The resulting protoplast suspension was centrifuged at 800 xg for 10 minutes.

The pellet was washed twice with 20 ml of tris buffer (pH 7.2, 0.05 M) containing 0.65 M mannitol, 0.01 M MgSO$_4$, and 0.01 M KCl. Next the protoplast pellet was gently homogenized in a Teflon homogenizer at 4° C. After 2 ml of tris buffer had been added, the suspension was centrifuged at 1000 xg for 10 minutes. Approximately, 2.5 ml of liquid, cell-free extract is obtained per flask.

Since this extract itself contains precursor to cephalosporin, the addition of 5μ moles of adenosine triphosphate (ATP), 10μ moles of phosphoenolypyruvate (PEP), and 100μ grams of pyruvate kinase, followed by a 5 hour incubation at 25° C. and pH 7.2 produces cephalosporin. During production, it is necessary to effect oxygen transfer by shaking at 250 rpm on a rotary shaker having a two inch diameter orbit.

Various experiments resulted in findings that intact cells were not responsible for the reaction, that the reaction is energy dependent, and that no protein synthesis occurs during cephalosporin production.

Thus, the C. acremonium lysate, which contained some cell debris and oily particles which were not removed by the centrifugation at 1000 xg, was filtered through a size RA Millipore filter. Since no significant decrease in activity was observed when the filtrate was used in place of the unfiltered lysate, it was concluded that intact cells could not be responsible for the reaction.

The addition of ATP to the system was observed to increase the amount of cephalosporin produced. An ATP regeneration system comprising PEP and pyruvate kinase also increased cephalosporin production.

Addition of 1 mM of KCN resulted in complete inhibition of the reaction despite the addition of ATP. Lowering the agitation speed from 250 to 120 rpm inhibited cephalosporin production indicating that a high degree of oxygen transfer is necessary in order for the biosynthesis to occur. The inclusion of cycloheximide in the cell free system had no effect on cephalosporin production. Furthermore, the addition of L-α-aminoadipic acid, L-valine, and L-cysteine did not stimulate production. These observations are consistent with the facts that protein synthesis is not required and something quite different from the fermentation biosynthesis is occurring.

When a crude preparation of penicillin N was added to the system, cephalosporin production was markedly increased. On the other hand, penicillin G or 6-aminopenicillanic acid did not stimulate production. Since the penicillin N sample used in this experiment was only about 20% pure, it was treated with penicillinase until its antibacterial activity was destroyed. The treated sample showed no stimulation of cephalosporin production whatsoever.

That a cephalosporin antibiotic was in fact being produced was verified as follows. A mutant of *E. coli*, designated ESS, which is super-sensitive to β lactam antibiotics was seeded onto a plate of antibiotic medium No. 5 (Difco Laboratories, Detroit, Mich.) in the presence or absence of penicillinase or cephalosporinase. This mutant is about equal sensitive to known samples of cephalosporin C, deacetoxycephalosporin C, deacetylcephalosporin C, and penicillin N. After incubation at 37° C. for 18 hours, zones of incubation were measured. The amount of β lactam antibiotic that had been produced by the cellfree system was estimated by the increase in zone size during the five hour incubation with cell free products of the invention using a known sample of cephalosporin C as a standard. Cephalosporinase prepared from sonically-ruptured cells of *Enterobacter cloacae* was obtained from Dr. L. Fare of Smith, Kline, and French Laboratories, Philadelphia, Penn. This preparation attacks both the cephalosporins and penicillin N. Penicilinase (Difco) does not affect the antibiotic activity of cephalosporins but destroys penicillin N.

The drawing is a graph of the number of μg/ml of β lactam antibiotic(s) produced versus the incubation time in hours when assayed in the presence of penicilinase or in the presence of cephalosporinase. The reaction mixture in a final volume of 1 ml, in addition to the cell free extract, contained 5μ moles of ATP, and an ATP regeneration system comprising 10μ moles of PEP and 100 mg pyruvate kinase. The reaction mixture also contained 0.01 M KCl, 0.01 M $MgSO_4$, 0.64 M mannitol, and 0.05 M pH 7.2 tris buffer.

As shown in the drawing, the protoplast lysate synthesized one or more β lactam antibiotics which were resistant to penicillinase, indicating that the antibiotic produced was not penicillin N, but sensitive to cephalosporinase, indicating that the antibiotic or antibiotics produced had the 6-membered dihydrothiazine ring characteristic of the cephalosporin antibiotics. As can be further seen from the drawing, production of the cephalosporin(s) was linear for 3 hours and reached its maximum level at about 5 hours.

From the foregoing, it will be obvious to those skilled in the art that various modifications in the above described process could be made without departing from the spirit and scope of the invention. For example, it is obvious that although ATP is necessary for the reaction, cephalosporin(s) are produced whether or not an ATP regeneration system is added to the cell-free extract. Furthermore, although phosphoenolpyruvate and pyruvate kinase are the preferred phosphate donor and phosphotransferase enzyme for use in regenerating the ATP which drives the cell-free synthesis, it is clear that many other phosphate donors and transferase enzymes are operable and in fact that no ATP regeneration system at all be necessarily employed.

In addition to these modifications, it will be obvious to those skilled in the art that methods of producing the cell-free extract other than by treating the cells as disclosed herein will be possible. Specifically, it will be within the skill of those in the art to utilize other lysing enzymes, and indeed, other non-enzymatic methods of lysing the cell walls to produce the extract. Also, it is contemplated that enzymatically active fractions of the extract may be isolated, which fractions will show increased activity and be more productive of cephalosporin antibiotic.

In order to transfer sufficient oxygen, the foregoing exemplary procedures require vigorous shaking. However, other methods of providing high oxygen transfer will be usable. For example, the use of oxygen enrichment will alleviate the vigorous shaking requirement. Known methods may be employed to isolate the cephalosporin produced. The preferred isolation technique is disclosed in the *Journal of Fermentation Technology*, Vol. 54, No. 10, p. 683–695 (1976) (Kitano et al.). Briefly, the technique involves adsorbing cephalosporin from the culture filtrate on charcoal, elution with a 50% acetone aqueous solution; elution from acetate type Amberlite IRA-900 resin with 0.3 N sodium acetate, and elution from charcoal with 50% acetone. If the eluate is then subjected to column chromatography on cellulose using 70% n-propanol, substantially pure cephalosporins are eluted. If desired, the cephalosporin species, if more than one are present, may be fractionated by thin layer chromatography on cellulose with a 3:1:1 mixture of n-butanol, acetic acid, and water, followed by electrophoresis on paper using 10% acetic acid.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A process for producing a cephalosporin antibiotic, said process comprising the steps of:

providing a cell-free extract of *Cephalosporium acremonium*;

providing a source of starting material comprising a substance having the formula:

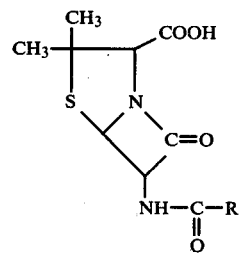

wherein R is a hydrocarbon containing 1–4 carbon atoms terminally substituted with a radical selected from the group consisting of carboxy, amino, and combinations thereof;

contacting the extract and the starting material in a reaction zone while promoting oxygen transfer;

providing ATP as an energy source to said reaction zone; and allowing a component of the extract to react with said precursor for a sufficient amount of time to produce a cephalosporin antibiotic.

2. The process as set forth in claim 1 wherein the ATP utilized in the cephalosporin antibiotic production is regenerated by an ATP regenerating system comprising a phosphate donor and a phosphotransferease enzyme.

3. The process as set forth in claim 2 wherein the phosphate donor is phosphoenolpyruvate and the phosphotransferase enzyme is pyruvate kinase.

4. The process as set forth in claim 1 wherein said cell-free extract is made by treating *Cephalosporium acremonium* cells with a lysing enzyme.

5. The process as set forth in claim 4 wherein said cell-free extract is made by treating *Cephalosporium acremonium* cells with endoβ(1→3) glucanase and endoβ(1→4) glucanase and zymolyase.

6. The process as set forth in claim 1 wherein high oxygen transfer is promoted by vigorously shaking the reaction components in the reaction zone.

7. The process as set forth in claim 1 wherein mannitol and trace concentrations of KCL and MgSO₄ are included in the reaction and the system is buffered to about pH 7.2.

8. The process as set forth in claim 1 wherein the starting material is selected from the group consisting of substances having the formula:

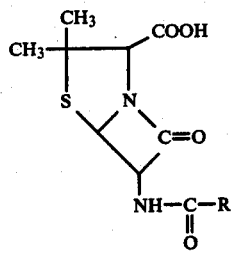

wherein R is selected from the group consisting of:

—(CH₂)₃—COOH

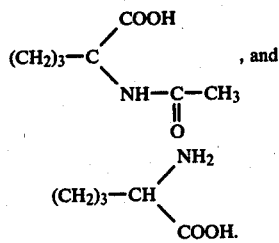

9. The process as set forth in claim 8 wherein R is

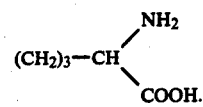

10. A process for producing a cephalosporin antibiotic, said process comprising the steps of:
providing a source of *Cephalosporium acremonium* mycelia;
treating said mycelia with lytic enzyme endoβ(1→3) glucanse, endoβ(1→4) glucanse and, from Arthrobacter, zymolyase;
incubating the treated mycelia to produce a protoplast suspension and homogenizing the suspension to produce a cell free extract;
providing a source of starting material selected from the group consisting of:

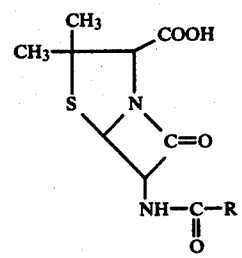

wherein R is:

—(CH₂)₃—COOH

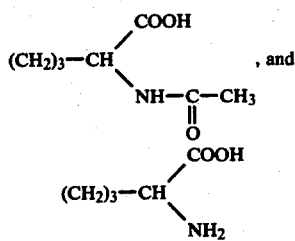

contacting the extract and the starting material in the presence of ATP in a reaction zone while promoting oxygen transfer; and
allowing a component of the extract to react with the starting material for a sufficient amount of time to produce a cephalosporin antibiotic.

* * * * *